(12) United States Patent
Grenacher et al.

(10) Patent No.: US 6,444,856 B2
(45) Date of Patent: Sep. 3, 2002

(54) PREPARATION OF ALDEHYDES AND/OR ALCOHOLS HAVING FROM 6 TO 30 CARBON ATOMS

(75) Inventors: Armin Volker Grenacher, Mutterstadt; Hans-Georg Hein, Worms; Hans Stepp, Gönnheim; Hans-Jürgen Fröhlich, Bissersheim; Willi Schönmann, Limburgerhof; Gerhard Borchert, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/867,574

(22) Filed: May 31, 2001

(30) Foreign Application Priority Data

Jun. 2, 2000 (DE) .......................................... 100 27 355

(51) Int. Cl.[7] .............................................. C07C 45/50
(52) U.S. Cl. ........................ 568/420; 568/454; 422/224

(58) Field of Search ................................. 568/451, 454; 422/224, 235

(56) References Cited

U.S. PATENT DOCUMENTS 3,830,846 A    8/1974    Duembgen et al. ......... 260/598

FOREIGN PATENT DOCUMENTS

GB         1079209         8/1967

*Primary Examiner*—Sreeni Padmanabhan
(74) *Attorney, Agent, or Firm*—Keil & Weinkauf

(57) ABSTRACT

In a process for preparing aldehydes and/or alcohols having from 6 to 30 carbon atoms by hydroformylation of olefins by means of synthesis gas in the presence of a catalyst at from 120° C. to 210° C. and pressures of from 100 to 400 bar, a reaction mixture comprising olefins, synthesis gas and catalyst or catalyst precursor is, according to the present invention, introduced at high velocity into a high-pressure reactor via a nozzle having an adjustable flow cross section.

10 Claims, 1 Drawing Sheet

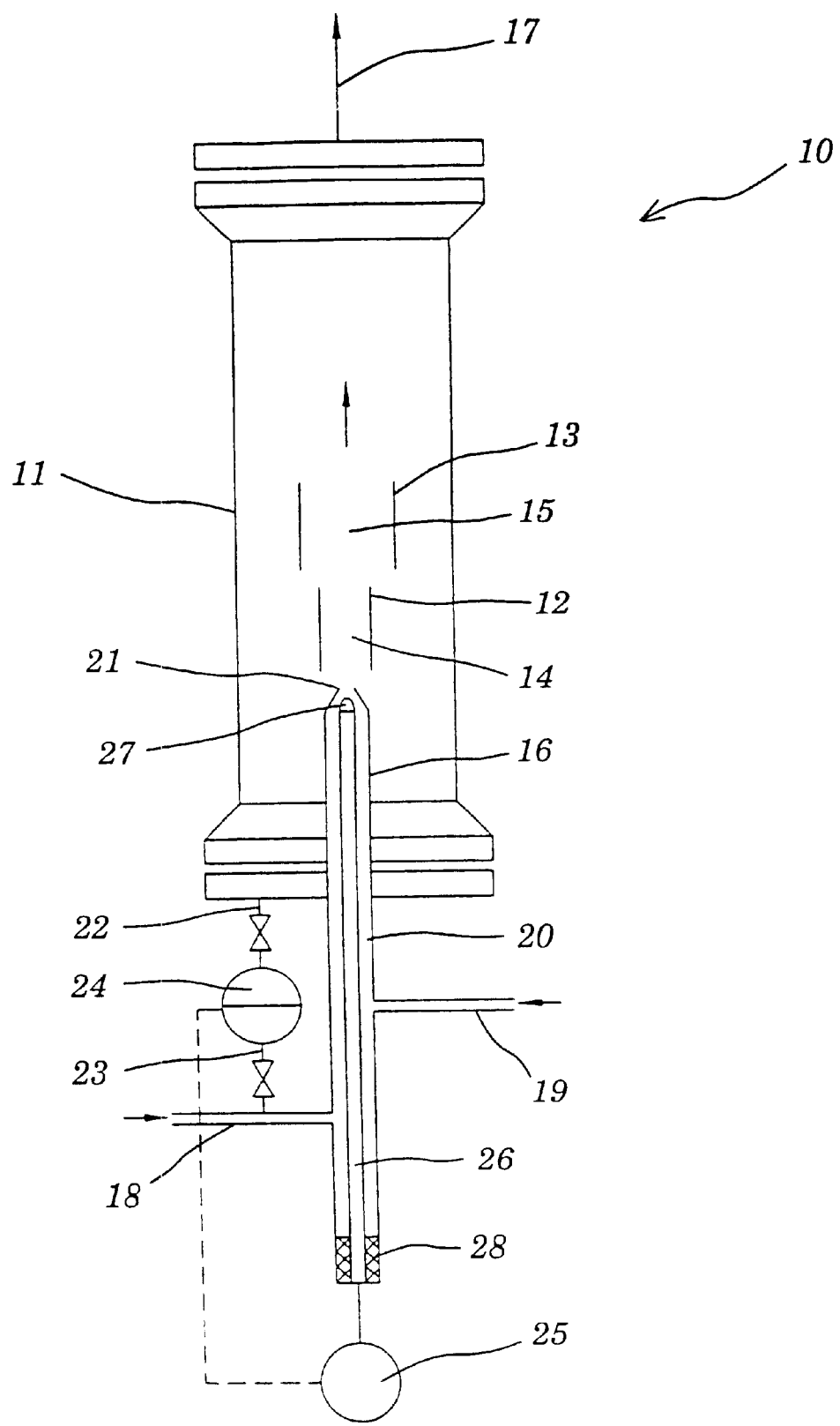
Fig.

PREPARATION OF ALDEHYDES AND/OR ALCOHOLS HAVING FROM 6 TO 30 CARBON ATOMS

The present invention relates to a process for preparing aldehydes and/or alcohols having from 6 to 30 carbon atoms by hydroformylation of olefins by means of synthesis gas in the presence of a cobalt catalyst at from 120 to 210° C. and pressures of from 100 to 400 bar, in which a reaction mixture comprising olefins, synthesis gas and catalyst or catalyst precursor, preferably aqueous cobalt salt solution, is introduced at high velocity into a high-pressure reactor. A liquid phase which, for example, consists of not yet reacted reaction mixture and aldehydes which have already been formed is present in the high-pressure reactor. In addition, the present invention relates to an improved hydroformylation reactor for preparing aldehydes and/or alcohols which comprises a high-pressure tube having at least one inlet nozzle for a reaction mixture and at least one outlet line for reaction products.

The hydroformylation of olefins by means of carbon monoxide and hydrogen in the presence of metal carbonyls of transition group VIII of the Periodic Table, for example cobalt or rhodium compounds, to form aldehydes having one more carbon atom is referred to as the oxo process. The aldehydes obtained in this way can be converted into the corresponding alcohols by subsequent hydrogenation. The oxo process is a widespread industrial method of preparing aldehydes and alcohols. A person skilled in the art therefore has a wide choice of proven methods of carrying out the oxo process (cf. J. Falbe, editor, "New Synthesis with Carbon Monoxide", Springer-Verlag, Berlin 1980). While lower olefins are now hydroformylated using virtually exclusively ligand-modified rhodium or cobalt catalysts, for example rhodium catalysts modified with phosphines, the oxo process using unmodified cobalt or rhodium catalysts still retains its dominant position in the reaction of higher olefins (i.e. olefins having more than 6 carbon atoms).

With the exception of unbranched olefins in the case of which retention of the linear structure in the hydroformylation is of great importance for the end products, the branched olefins which are readily obtainable by oligomerization of $C_3$- and/or $C_4$-olefins are hydroformylated industrially virtually exclusively by means of unmodified cobalt carbonyls, i.e. in the absence of ligands. This catalyst system is not only very cheap, but is also universally usable. Furthermore, compared to rhodium catalsyts, cobalt catalysts give higher yields of the particularly sought-after linear aldehydes starting from the same olefin.

The reaction of olefins with carbon monoxide and hydrogen to form aldehydes and alcohols proceeds exothermically. When this reaction is carried out continuously on an industrial scale, it is therefore necessary to take steps to ensure that the heat of reaction is distributed uniformly in the reaction mixture and removed. Local temperature peaks, which lead to undesirable secondary and subsequent reactions, have to be substantially avoided. In addition, it has to be ensured that the liquid starting materials are well mixed with the gaseous starting materials so that the reaction proceeds in the stoichiometric ratio.

The processes which are used industrially at present differ essentially in the form in which the cobalt carbonyls are made available to the hydroformylation reactor and the way in which the catalyst is removed from the reaction mixture after the hydroformylation and is returned to the process with very small losses.

A proven method is the use of aqueous solutions of cobalt salts of lower carboxylic acids, preferably cobalt formate or cobalt acetate. Under the conditions prevailing in the reactor, the Co(II) salts are rapidly converted into the actual hydroformylation catalyst, namely hydridocobalt tetracarbonyl ($HCo(CO)_4$). The hydroformylation occurs in a high-pressure reactor in which an intimate mixture of olefin, catalyst complex and synthesis gas is present at from 120 to 210° C. and pressures of from 100 to 400 bar. After the olefin has been reacted, the cobalt carbonyls homogeneously dissolved in the organic phase can be converted back into Co(II) compounds by a valence change on the central atom by means of oxidizing substances and thus made heterogeneous. The Co(II) compounds are extracted from the organic reaction product using a weakly acidic, aqueous phase, so that after phase separation the organic phase is virtually cobalt-free and can be passed directly to further processing.

The aqueous solution of cobalt salts can, with or without prior concentration, be returned directly as catalyst precursor to the high-pressure reactor or be used as uptake medium in the oxidation of the output from the reactor.

Processes in which the preparation of the catalyst complex, known as precarbonylation, the extraction of the resulting catalyst complex from the aqueous phase into the organic, olefin-containing phase and the hydroformylation of the olefin are carried out in separate process steps are known. Less complicated in terms of apparatus and therefore more economical is a single-stage process in which the formation of the catalytically active cobalt carbonyls from the aqueous cobalt salt solution and the hydroformylation of the feed olefin are carried out directly in the high-pressure reactor in a type of single-vessel reaction. The presence of aqueous phase in the reactor has the effect of increasing the yield, since subsequent reactions of the aldehydes initially formed, e.g. acetal formation or enal formation, are suppressed. As a result, no additional work-up steps for redissociating undesirable high boilers are necessary.

Among the prerequisites for an effective single-stage oxo process in a high-pressure reactor are that, firstly, the aqueous cobalt salt solution is dispersed very finely in the liquid olefin and that, secondly, intimate mixing with the synthesis gas introduced takes place.

Against the background of these conditions, DE 1 205 514 A describes a process in which at least part of the reactants are introduced at high velocity into a high-pressure reactor via a plurality of nozzles. The high-pressure reactor has a tubular construction and in its interior has internals, for example guide tubes, which make circulation of the reaction mixture possible. The circulation is maintained by the momentum of the reactants injected into the reaction mixture. According to DE 1 205 514 A, starting olefin and catalyst solution are injected. DE 1 938 102 A describes a similar process in which the reactants, i.e. the gaseous starting materials, the starting olefin and the catalyst solution are introduced through a single nozzle into the reaction product circulating in the high-pressure reactor. Here, the reactants are introduced into a mixing zone which is arranged in a cascade-like fashion in the reaction zone and extends in the entry direction of the reactants. The mixing zone can be realized by means of cylindrical or cone-shaped reactor internals having a defined diameter/length ratio. It allows a higher olefin throughput without losses in conversion and, owing to the good mixing, leads to smaller temperature gradients and therefore to reduced high boiler formation.

DE 1 938 102 A proposes introducing the reaction mixture into the high-pressure reactor at a nozzle exit velocity of from 10 to 100 m/s, in particular from 10 to 60 m/s. However, fluctuations in the feed streams, i.e. the introduction of the reaction mixture into the reactor, can occur in operation. The causes of these can be changed external circumstances, for instance nonuniform acceptance of aldehyde or alcohol on the part of the plant carrying out further processing. In addition, other starting olefins can make a change in the throughput necessary.

To be able to maintain the preferred nozzle exit velocity of from 10 to 60 m/s even when the throughput changes, part of the contents of the reactor are recirculated to the feed stream by means of an external circulation pump in the process described in DE 1 938 102 A. Under the conditions prevailing in the high-pressure oxo process using unmodified cobalt carbonyls, i.e. at from 120 to 210° C. and pressures of from 100 to 400 bar, such external pumps need to have a very expensive construction, particularly in respect of the shaft seal and the corrosion resistance. In addition, the catalyst complex, namely hydridocobalt tetracarbonyl, tends to decompose with precipitation of solid, which can lead to impairment of or even damage to the circulation pump.

It is an object of the present invention to provide a process for preparing aldehydes and/or alcohols having from 6 to 30 carbon atoms by hydroformylation of olefins by means of synthesis gas in the presence of a cobalt catalyst at from 120° C. to 210° C. and pressures of from 100 to 400 bar, in which the starting materials for the reaction are introduced at a velocity of from 10 to 80 m/s, preferably from 50 to 70 m/s, into a high-pressure reactor, where this entry velocity can be maintained without additional external circulation pumps even when the throughput changes.

We have found that this object is achieved by the process as claimed in claim 1, in which the reaction mixture is introduced into the reactor via a nozzle having an adjustable flow cross section. Accordingly, the present invention proposes altering the free flow cross section of the nozzle as a function of the feed flow, i.e. the throughput of reaction mixture, in such a way that a constant optimum exit velocity of the reaction mixture from the nozzle into the high-pressure reactor is always maintained. This ensures intimate mixing of the reactants and consequently a largely stoichiometric cobalt-catalyzed hydroformylation of olefins having more than 6 carbon atoms at constant high yield even when the throughput changes.

In a preferred variant of the process of the present invention, the flow cross section of the nozzle is regulated as a function of the differential pressure between the nozzle inlet and the nozzle outlet, i.e. the pressure drop through the nozzle is employed as regulating parameter. Such a differential pressure measurement can be carried out in a simple manner. Under the conditions prevailing in the reactor, it is found to be particularly advantageous to maintain an essentially constant differential pressure in the range from 5 to 15 bar, preferably in the range from 8 to 12 bar. A differential pressure of 10 bar, which then corresponds to an exit velocity of the reaction mixture of about 60 m/s, is very particularly preferred. In a relatively simple embodiment of the process of the present invention, a regulator is employed to ensure that the differential pressure is always within the abovementioned pressure range. However, particular preference is given to determining the differential pressure which is optimum for a particular reactor and particular reaction conditions, i.e., for example, a differential pressure of 10 bar, and the pressure regulator is designed so that this pressure is kept constant to within a certain maximum deviation, for example a deviation of ±5%. As an alternative to pressure regulation of the flow cross section of the nozzle, it would also be conceivable, for example, to employ the exit velocity of the reaction mixture or the mass or volume flow of the reaction mixture as control parameter for regulating the flow cross section.

A person skilled in the art will be familiar with a wide variety of possible ways of realizing a nozzle having an adjustable flow cross section. For example, the interior of the nozzle can be provided with mechanically alterable orifice plates or baffles or deflecting plates which can be swiveled from the inner wall to the center of the nozzle. According to the present invention, the flow cross section of the nozzle is preferably adjusted by means of the nozzle outlet orifice having an alterable open cross section. Here too, various possible ways of achieving the alterable open cross section are conceivable, for example orifice plates or swivelable, overlapping lamellae. The open cross section of the outlet orifice of the nozzle is particularly preferably adjusted by means of an axially movable cone located within the nozzle upstream of the outlet orifice. The nozzle cross section advantageously tapers conically to the outlet orifice. The movable cone then advantageously has a shape which essentially complements the inner surface of the conical nozzle outlet. If the cone is pushed from a drawn-back position along the nozzle axis in the direction of the outlet orifice, this reduces the open cross section of the latter and thus reduces the flow cross section of the nozzle. If, for example, the throughput of reaction mixture is decreased, for instance because less aldehydes are being accepted by the plants carrying out further processing, the flow resistance in the nozzle can be increased in this way and the pressure which decreases through the nozzle can thus be kept constant.

The cone is preferably moved pneumatically. Thus, the nozzle can be provided with an external pneumatic drive which acts on the cone via a movable spindle which is inserted into the nozzle through a seal. The cone can in this case be realized as a conical or tapered end of the spindle.

The present invention also provides a hydroformylation reactor for preparing aldehydes and/or alcohols comprising a high-pressure tube having at least one inlet nozzle for a reaction mixture and at least one outlet line for reaction products, wherein the inlet nozzle has an adjustable flow cross section.

The inlet nozzle preferably has an outlet orifice which opens into the high-pressure tube and whose open cross section can be adjusted by means of adjusting devices, which are actuated by a differential pressure regulator. The adjusting devices can include an axially movable cone located upstream of the outlet orifice. The exit cross section available for the reactants can be adjusted via the position of the cone as a function of the throughput of reaction mixture so that the reactants leave the nozzle at a velocity of from 10 to 80 m/s, preferably from 30 to 70 m/s and particularly preferably about 60 m/s. However, the exit velocity or the throughput is preferably not itself employed as regulating parameter, but rather the pressure drop through the nozzle is measured and kept essentially constant within the range from 5 to 15 bar, preferably from 8 to 12 bar, by adjustment of the cone.

The cone is advantageously located on the end face of a spindle which is in turn actuated by a pneumatic drive.

One or more mixing zones defined by internals, as known from DE 1 938 102 A, is/are preferably provided in the high-pressure tube.

The aldehydes and alcohols prepared by the process of the present invention or using the apparatus of the invention are suitable for, in particular, the preparation of solvents, polymer plasticizers and surfactants.

BRIEF DESCRIPTION OF THE DRAWING:

The invention is described in more detail below with the aid of an illustrative embodiment shown in the accompanying drawing.

The figure schematically shows a longitudinal section through a hydroformylation reactor according to the present invention. The hydroformylation reactor 10 comprises a vertical high-pressure tube 11 in which internals 12, 13 defining mixing zones 14, 15 are installed. A nozzle 16 projects into the reactor from the bottom. A mixture of reaction product which has already been formed, i.e. for example aldehydes, and not yet reacted reactants circulates in the reactor. The reaction product leaves the high-pressure tube 11 at its upper end via an outlet line 17 which is shown schematically. The reactants olefin, oxo gas and aqueous cobalt formate solution are fed in through lines 18, 19 which are under appropriate pressure. These lines open into the shaft 20 of the nozzle 16. The reaction mixture flows through the nozzle shaft 20 and leaves the nozzle 16 at high velocity through an outlet orifice 21 opening into the reaction region of the high-pressure tube 11. A differential pressure is established between nozzle inlet and nozzle outlet and this is measured via schematically shown pressure lines 22, 23 between the feed line 18 for olefin and oxo gas and the lower part of the high-pressure tube 11. The differential pressure is kept essentially constant by means of a regulator 24. For this purpose, the regulator 24 controls a pneumatic adjusting drive 25 which actuates a spindle 26 which ends in a cone 27 at the end farthest from the actuating mechanism. The spindle 26 with the cone 27 can be moved axially by means of the pneumatic drive 25. The cone 27 can alter the open cross section or flow cross section of the conical outlet orifice 21 of the nozzle 20 so that the pressure drop through the nozzle and thus the exit velocity of the reactants remain essentially constant when the throughput changes. The spindle 26 is sealed against the high-pressure tube 11 by means of a seal 28 provided at the drive end of the spindle.

Since the reaction proceeds exothermically, the high-pressure tube 11 usually has facilities for removing the heat of reaction (not shown here in the interest of clarity).

The advantages of the invention are illustrated below by means of examples.

EXAMPLE 1

A hydroformylation reactor as shown schematically in the figure is used. A vertical high-pressure tube having a diameter of 1 m and a length of 18 m and fitted with appropriate internals for heat removal is provided with a single-fluid nozzle whose free open cross section can be altered and which opens into the reactor 46 cm above the bottom. Downstream of the nozzle there are concentrically arranged mixing and after-mixing zones whose dimensions correspond to the relationships described in DE 1 938 102 A.

Installed downstream of the high-pressure tube in the form of a cascade is a second high-pressure tube having a diameter of 0.8 m and a height of 12 m which has no nozzle at the inlet and no internals for mixing and through which the reaction mixture flows from the bottom upward.

The single-fluid nozzle in the first high-pressure tube has a diameter of 13 mm at the mouth of the nozzle and this can be narrowed steplessly down to an annular flow cross section of 20 mm$^2$ by pushing in a valve cone.

5,000 kg/h of an octene isomer mixture, 2,900 standard m$^3$/h of oxo gas (molar ratio of CO:H$_2$=1:1.5) and 500 l/h of an aqueous cobalt formate solution (cobalt content=1.3% by weight) are fed to this nozzle.

At this throughput, the spindle with the cone is moved vertically by means of the pneumatic drive so that the optimum differential pressure of 10 bar is established through the nozzle.

A pressure of 275 bar and a temperature of 187±1.5° C. are maintained in the first high-pressure tube; the reaction conditions in the second high-pressure tube differ only insignificantly therefrom.

6,400 kg/h of a crude C$_9$ oxo product comprising 86% by weight of C$_9$-aldehydes and C$_9$-alcohols together with 7% by weight of hydrocarbons and 7% by weight of high boilers are obtained. Hydrogenation and distillation gives 5,500 kg/h of pure C$_9$-alcohol, which corresponds to an alcohol yield of 85.5% of the amount which is theoretically obtainable from the octene mixture used.

EXAMPLE 2

In the same apparatus as in Example 1, the octene throughput is reduced to 60% of the amount in Example 1. At the same time, the free flow cross section of the nozzle is narrowed by means of the adjustable cone until a differential pressure of 10 bar has been established again. The yield of C$_9$-alcohol remains unchanged compared to Example 1.

EXAMPLE 3

(Comparative Example)

The apparatus and throughput correspond to Example 2, but the full nozzle cross section is retained by not actuating the cone. The measured differential pressure drops to about 3 bar. The yield of C$_9$-alcohol drops by 2% with a similar increase in the by-products.

We claim:

1. A process for preparing aldehydes and/or alcohols having from 6 to 30 carbon atoms by hydroformylation of olefins by means of synthesis gas in the presence of a catalyst at from 120° C. to 210° C. and pressures of from 100 to 400 bar, comprising introducing a reaction mixture comprising olefins, synthesis gas and catalyst or catalyst precursor at high velocity, into a high-pressure reactor via an inlet nozzle having an adjustable flow cross section, monitoring the throughput of the reaction mixture thought the inlet nozzle, maintaining a constant exit velocity of the reaction mixture from the inlet nozzle into the high-pressure reactor by adjusting the flow cross section of the nozzle.

2. A process as claimed in claim 1, wherein the flow cross section of the nozzle is regulated as a function of the differential pressure between nozzle inlet and nozzle outlet.

3. A process as claimed in claim 2, wherein a differential pressure of from 5 to 15 bar is kept essentially constant by regulating the flow cross section.

4. A process as claimed in claim 1, wherein the flow cross section of the nozzle is adjusted by means of an axially movable cone located upstream of an outlet orifice of the nozzle.

5. A process as claimed in claim 4, wherein the cone is moved pneumatically.

6. A hydroformylation reactor for preparing aldehydes and/or alcohols comprising a high-pressure tube having at least one inlet nozzle for a reaction mixture and at least one outlet line for reaction products, wherein the inlet nozzle has an adjustable flow cross section.

7. A hydroformylation reactor as claimed in claim 6, wherein the inlet nozzle has an outlet orifice which opens into the high-pressure tube and whose open cross section can be adjusted by means of adjusting devices, which are actuated by a differential pressure regulator.

8. A hydroformylation reactor as claimed in claim 7, wherein the adjusting devices include an axially movable cone located upstream of the outlet orifice.

9. A hydroformylation reactor as claimed in claim 8, wherein the adjusting devices also include a pneumatic drive which is coupled to the cone via a spindle.

10. A hydroformylation reactor as claimed in claim 9, wherein one or more mixing zones are provided in the high-pressure tube.

* * * * *